United States Patent [19]

Vanlerberghe et al.

[11] Patent Number: 5,306,488
[45] Date of Patent: Apr. 26, 1994

[54] COSMETIC COMPOSITION FOR THE HAIR CONTAINING A WAX MICRODISPERSION AND A PROCESS FOR TREATING THE HAIR USING THE COMPOSITION

[75] Inventors: Guy Vanlerberghe, Montjay-la-Tour; Luc Nicolas-Morgantini, Rully; Alain Lety, Lagny-sur-Marne, all of France

[73] Assignee: L'Oreal, Paris, France

[21] Appl. No.: 483,378

[22] Filed: Feb. 23, 1990

[30] Foreign Application Priority Data

Feb. 24, 1989 [LU] Luxembourg .......................... 84 457

[51] Int. Cl.$^5$ .............................................. A61K 7/075
[52] U.S. Cl. ......................................... 424/71; 424/70
[58] Field of Search ........................ 424/401, 70, 59; 513/937; 514/943, 938; 252/186

[56] References Cited

U.S. PATENT DOCUMENTS

| | | | |
|---|---|---|---|
| Re. 29,871 | 12/1978 | Papantoniou | 514/943 |
| 4,146,499 | 3/1979 | Rosano | 252/186.25 |
| 4,284,630 | 8/1981 | Yu | 514/943 |
| 4,379,755 | 5/1983 | Yamada | 514/943 |
| 4,468,254 | 8/1984 | Yokoyama et al. | 106/271 |
| 4,677,232 | 6/1987 | Sebag | 424/47 |
| 4,775,526 | 10/1988 | Lang et al. | 424/59 |
| 4,798,682 | 1/1989 | Ansmann | 252/312 |
| 4,948,584 | 8/1990 | Brand | 424/70 |
| 4,950,467 | 8/1990 | Phalanges | 424/61 |
| 4,952,391 | 8/1990 | Lang | 424/45 |

FOREIGN PATENT DOCUMENTS

| | | |
|---|---|---|
| 0045008 | 2/1982 | European Pat. Off. . |
| 0101007 | 2/1984 | European Pat. Off. . |
| 0167825 | 1/1986 | European Pat. Off. . |
| 0283247A2 | 3/1988 | European Pat. Off. ........ C08J 3/02 |
| 0283247 | 9/1988 | European Pat. Off. . |
| 1794088 | 7/1971 | Fed. Rep. of Germany . |
| 1464228 | 12/1966 | France . |
| 2222998 | 10/1974 | France . |
| 2542008 | 9/1984 | France . |

*Primary Examiner*—Thurman K. Page
*Assistant Examiner*—R. Harrison
*Attorney, Agent, or Firm*—Cushman, Darby & Cushman

[57] ABSTRACT

A cosmetic composition for the hair contains a wax dispersion in a liquid vehicle. The dispersed phase is a stable microdispersion of particles of wax having a size lower than 500 nm and an end melting point greater than 60° C. and lower than 100° C. The composition contains from 0.1 to 40 weight percent wax, form 0.01 to 25 weight percent anionic or nonionic emulsifier and at least 35 weight percent water. The composition does not contain a cationic surfactant.

19 Claims, No Drawings

COSMETIC COMPOSITION FOR THE HAIR CONTAINING A WAX MICRODISPERSION AND A PROCESS FOR TREATING THE HAIR USING THE COMPOSITION

The present invention relates to a cosmetic composition or a cosmetic composition support for the hair comprising a wax microdispersion, as well as to a process for the cosmetic treatment of the hair using said composition.

It is known that waxes, whose use in cosmetology is very old, are natural substances (animal or vegetable) or synthetic substances, which are solid at ambient temperature (21 degrees C); which generally have a certain plasticity; which are insoluble in water and are soluble in oils; and which are capable of forming water repellant films. With respect to the definition of waxes and their uses in cosmetology, mention can be made for example of P. D. Dorgan, Drug and Cosmetic Industry, December 1983, pages 30–33, and the Handbook of Cosmetic Science, H. W. Hibbot ed., Pergamon Press, Oxford (1963), page 60. In capillary preparations, the most classic use is that of semi-solid preparations called pomades for the hair or solid brillantines. In such compositions, the waxes are used in admixture, principally, with significant amounts of various oils; see for example E. W. Flick, "Cosmetic and Toiletry Formulations", Ed. Noyes Publications, New Jersey, U.S.A. (1984) pages 271–288.

In German patent application 3.534.733, there is described foaming and clear cosmetic compositions containing an oil and, optionally, from 0.05 to 1 percent wax. In these compositions, the oil, the optionally present wax are solubilized. The presence of the oil and/or the wax in these compositions have for a purpose to re-oil the skin and thus avoid depleting to a too significant degree the skin's oil, which depletion is caused by the use of anionic surfactants.

It is also known that it is possible to obtain microemulsions with certain oils and microdispersions with certain waxes, which are stable and dilutable with water without limitation and without aggregation and sedimentation of the particles in suspension. The wax microdispersions are obtained by melting the wax in the presence of an anionic or non-ionic surfactant, and optionally with a portion of the water. Thereafter hot water, with stirring, is progressively added. The intermediate formation of a water-in-oil type emulsion is observed, followed by a phase inversion with the final production of an oil-in-water type emulsion. On cooling, a stable microdispersion of solid colloidal particles of wax is obtained, see for example, "Microemulsion Theory and Practice", L. M. Prince Ed., Academic Press (1977), pages 21–32.

These wax microdispersions are used principally to make leather articles shiny and for plastic coverings for soil.

It has now been discovered that such wax microdispersions can be used principally as hair styling lotions which impart volume to the hair style, and also thicken the hair, principally fine and soft hair. These lotions provide hair which is controlled and sheathed up to their tips, thereby rendering the hair smooth or glossy. They also exhibit the surprising property of not imparting to the hair an oily appearance but, to the contrary, they delay the onset of such an oily aspect although they contain wax as a principal active ingredient, that is to say a substance classified as a fatty material.

The present invention thus relates to a cosmetic composition or a cosmetic composition support for the hair comprising a fluid, non-foaming composition containing a wax dispersion in a liquid vehicle, the dispersed phase of which is a stable microdispersion of particles having a size lower than 500 nm, the said particles consisting essentially of a wax or a mixture of waxes, the said wax or the said mixture of waxes having a end melting point greater than 60° C. and lower than 100° C. and being capable of forming a microdispersion such as that defined above, the said composition containing, by weight, from 0.1 to 40 percent of wax, from 0.01 to 25 percent of at least one nonionic or anionic emulsifying agent and at least 35 percent of water, the wax/emulsifying agent weight ratio ranging from 1 to 30.

The wax or mixture of waxes, employed in accordance with the present invention, must then be capable of giving, in combination with the nonionic and/or anionic emulsifying agent, in accordance with the process described above, stable microdispersions having particle sizes lower than 500 nm. The useful waxes or mixtures of waxes can be selected by simple routine experimentation. However, the wax microdispersion according to the invention cannot contain a cationic surfactant.

In particular embodiments of the present invention, the composition employed can also exhibit the following characteristics taken alone or in combination:

the wax is a wax selected from Carnauba wax, Candelilla wax, Alfa wax and mixtures thereof;

the wax contains, in addition to Carnauba wax or Candelilla wax or mixtures thereof, another wax or a mixture of other waxes, for example, paraffin wax, ozokerite, hydrogenated jojoba wax, rice wax, beeswax optionally esterified, or a ceramide; the weight proportion of Carnauba wax and/or Candelilla wax, in such mixtures, is preferably greater than or equal to 50 percent;

in the cosmetic compositions, the amount of wax is, for example, from 0.1 to 20 percent, principally from 1 to 20 percent, and in particular from 1 to 10 percent;

the emulsifying agent is present in a concentration ranging from 0.1 to 10 percent;

the said nonionic emulsifying agent is a polyalkoxylated and/or polyglycerolated surface active agent;

the said emulsifying agent is an anionic surface active agent;

the liquid vehicle contains from 80 to 100 percent of water, relative to the weight of the liquid phase;

the liquid vehicle consists of water;

at least one amphiphilic compound (non-emulsifying with respect to the waxes) such as cholesterol and fatty alcohols containing at least 12 carbon atoms, and the like can be combined with the wax; the concentration of the amphiphilic compounds can range up to 30 percent (principally up to 10 percent) by weight with respect to the wax or mixture of waxes;

an oil or a mixture of oils (principally those which are mentioned in the experimental portion hereafter), can be combined with the wax; the concentration of the oil can range up to 30 percent (principally up to 10 percent) by weight relative to the wax or mixture of waxes; preferably, however, the compositions in accordance with the present invention, are those which do not contain an oil:

the composition can also contain, depending upon the situation, at least one liposoluble active ingredient; representative liposoluble active ingredients, include, principally, liposoluble dyes or soluble sunscreen agents (substances capable of protecting the skin and/or hair against the harmful effects of ultraviolet radiation);

the concentration of the liposoluble active ingredients, when they are present, can range up to 30 percent (generally up to 10 percent) by weight relative to the weight of the wax or mixture of waxes;

the weight proportion of wax, and of the non-emulsifying amphiphilic compounds optionally present, in the particles is generally greater than 90 percent, relative to the weight of the particles, and is most often greater than 95 percent, the remainder comprising oils and/or liposoluble ingredients optionally present (not including emulsifying agents);

the weight ratio of wax/emulsifying agent can vary from 1 to 20 and principally from 2 to 10.

The vegetable waxes of Carnauba (extract of Copernicia Cerifera), of Candelilla (extract of Euphorbies Cerifera and of Pedilantus Pavonis), and of Alfa (extract of Stipa Tenacessima) are commercial products.

It is also possible to prepare cosmetic compositions or cosmetic composition supports by using commercial mixtures of self-emulsifiable waxes containing the Wax and the emulsifying agents. There can be employed, for example, wax sold under the trade name "CIRE AUTO LUSTRANTE OFR" by Tiscco, Bobigny, France, which contains Carnauba wax and paraffin wax, in combination with nonionic emulsifying agents, or the self-emulsifiable wax sold under the trade name "CERAX A.0. 28/B" by La Ceresine, Marseille, France, which contains Alfa wax in combination with a nonionic emulsifier. These commercial mixtures permit the preparation of wax microdispersions by the addition of water in accordance with the process described above.

The are the principal lipid constituents in the intercorneocytol spaces of the corneum stratum. They have been described, in particular, by Downing in Science, 1982, pages 1261-2, vol. 18. The ceramides are employed principally in cosmetic compositions as anti-aging agents and as hydrating agents; see for example Japanese patent application 87.176907. In capillary compositions they act as agents to protect the hair, see for example European patent application 0278505.

The ceramides ar difficult to disperse in cosmetic compositions. However, because of the present invention, it is possible to disperse them in large amounts.

Liposoluble dyes, optionally present in the composition of the present invention are, for example:

1-nitro-3-amino-4-isopropyl aniline,
1-nitro-2-methyl-3-methylamino-4-methyl aniline,
3-nitro-4-butylamino phenol,
4-hydroxy-3-methyl phenylazo benzene, and the product having the formula:

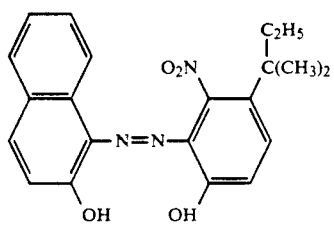

Representative liposoluble sunscreen agents, optionally present in the compositions of the present invention, include principally the following commercially available compounds:

3-benzylidene-d, 1-camphor,
3-(4'-methylbenzylidene)-d,1-camphor,
amyl 4-(dimethylamino) benzoate,
amyl and isoamyl p-methoxycinnamate and methyl salicylate.

One of the advantages of the composition of the present invention is that it permits the use of these liposoluble ingredients in an aqueous medium.

The anionic surfactants employed have, preferably, a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms and being able to have a double bond as in the case of oleic acid; the alkaline salts or salts of organic bases of alkyl-sulfuric and alkyl-sulfonic acids having 12 to 18 carbon atoms, of alkyl-arylsulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene.

All these anionic surfactants are well known and many among them are commercial products.

The nonionic surfactants are principally fatty acids or amides of polyalkoxylated and/or polyglycerolated fatty acids; the esters of fatty acids and polyalkoxylated and/or polyglycerolated polyols; fatty alcohols or polyalkoxylated and/or polyglycerolated alkylphenols; or polyalkoxylated and/or polyglycerolated 1,2- or 1,3-alkanediols; and alkylethers of polyalkoxylated and/or polyglycerolated 1,2- or 1,3-alkanediols or alkenediols. The fatty acids or alcohols, optionally unsaturated, have for example, 12 to 24 carbon atoms; the alkyl chain of the alkylphenols has, for example, 6 to 16 carbon atoms; the alkanediols or alkenediols have from 9 to 24 carbon atoms; the alkyl moiety of the alkylethers has from 4 to 20 carbon atoms; and the number of oxyalkylene units or ($CH_2CHOHCH_2O$) units can range from 2 to 40.

The polyalkoxylated nonionic derivatives are principally polyoxyethylenated derivatives, optionally polyoxypropylenated derivatives.

The polyalkoxylated fatty acids are commercial products, and are principally products sold under the mark "Myrj".

The esters of fatty acids and polyoxyethylenated polyols for which the polyol is sorbitol are known products (Polysorbate and products sold under the mark "Tween").

The polyoxyethylenated fatty alcohols are commercial products and principally those sold under the mark "Brij".

The polyglycerolated fatty alcohols, the polyglycerolated alkanediols or alkenediols, or the alkylethers of polyglycerolated alkanediols on alkenediols can be prepared, for example, in accordance with the processes described in French patents Nos. 1.477.048, 2.025.681, 2.091.516 and 2.465.780, or in accordance with analogous processes.

The fatty acids or amides of polyglycerolated fatty acids are principally described in French patent 1.484.723 or are also commercial products such as those sold under the mark "Plurol" (Gattefosse) or "Drewpol" (Stefan Company).

The cosmetic composition obtained in accordance with the present invention can also contain one or more conventional secondary ingredients such as thickening agents, stabilizers, perfumes or preservatives.

Compositions without a thickening agent are fluid lotions. Compositions with a thickening agent are lotions or fluid gels.

The thickening agents are more particularly selected from polyacrylic acids crosslinked with a polyfunctional agent, such as products sold under the trade name "Carbopol" by Goodrich, for instance "Carbopols 910, 934, 934P, 940, 941 and 1342", or cellulosic derivatives such as hydroxymethylcellulose, carboxymethylcellulose, hydroxybutylcellulose, hydroxypropylcellulose and more particularly hydroxyethylcellulose, including such products sold under the trade name "Natrosol" (150, 250) by Hercules or "Cellosize" (QP and WP) by Union Carbide, methylhydroxypropyl cellulose, in particular products sold under the trade name "Methocel" (E,F, J and K) by Dow Chemical or heterobio-polysaccharides such as, for example, xanthan gums sold under the mark "Keltrol" and "Kelan" by Kelco, "Rhodopol" and "Rhodigel" by Rhone Poulenc, or "Actigum" by Ceca/Satta.

When thickening agents are used they are preferably selected from the "Carbopols" and are employed, preferably, in an amount such that the viscosity of the composition is at most 25 poises (or 2.5 Pa.s) at about 25° C. (Contraves viscometer; measurement means No. 3; 10 minute rotation time at 200 rpm).

The useful perfumes are conventional perfumes, soluble in wax or dispersible or soluble in water. In particular they are those which are dispersible or soluble in water and are generally employed in an amount not exceeding 5 percent by weight.

Representative stabilizers include the phosphoric esters of fatty alcohols. They are generally employed in an amount lower than 1 percent by weight.

The preservatives are, for example, parahydroxybenzoic acid, its salts and esters, sorbic acid and its salts, dimethyloldimethylhydantoin and the derivatives of imidazolidinyl urea. They are employed in conventionally effective amounts.

The pH of the compositions obtained in accordance with the present invention can range from 3 to 10. The pH can optionally be adjusted using a conventional pH modifying agent.

The present invention also relates to wax microdispersions, such as defined above, in the preparation of a non-foaming, fluid cosmetic composition such as described above.

The compositions in accordance with the present invention are obtained by forming in a heated state a microemulsion. More precisely, these compositions are obtained by a process principally characterized by the fact that the wax and the emulsifier are heated to a temperature greater than the melting temperature of the wax but not greater than 100° C., optionally in the presence of one part of water, to completely melt the wax. Thereafter, water or the remainder of the water, at essentially the same temperature, is progressively added, with stirring, so as to form a wax microemulsion in a continuous aqueous phase. On cooling to ambient temperature a wax microdispersion is obtained.

The secondary ingredients, optionally present in the composition, are added according to the situation either with the starting products or to the completed composition.

The non-volatile hydrosoluble ingredients can optionally be added with the water employed to produce the microdispersion.

The liposoluble ingredients are generally added to the wax before producing the microdispersion.

The compositions obtained in accordance with the present invention can principally be employed as hair styling lotions and also as lotions to improve the appearance of the hair of persons having oily hair.

The compositions can be applied to dry or moistened, clean or soiled hair, and also before or after a shampoo. They can be rinsed or non-rinsed and can be applied daily.

When the compositions are applied before or after a shampoo, the application being followed or not by rinsing with water, they control the hair and impart hold and volume to the hair style. Moreover, the composition delays a hair re-oiling phenomenon which is observed with persons having oily hair.

To avoid this re-oiling phenomenon the composition of the present invention can be applied to hair which is dried after washing, and in particular on the portion of the hair near the roots. In this case, the composition is not rinsed off. It is observed that, notwithstanding the absence of a rinse, the composition does not impart to the hair a sticky feel and does not cause a gluing phenomenon of the hair.

Notwithstanding, the presence of a wax in the composition of the present invention, no oily appearance is imparted to the hair, even in the absence of rinsing. Moreover, notwithstanding the presence of a significant amount of water in the composition, drying the hair poses no problems and is effected rapidly.

When the composition contains a liposoluble coloring agent, the composition can be employed as a hair dye composition.

The compositions in the form of gels are used as hair styling gels.

It is also appropriate to note that the cosmetic composition supports, in accordance with the present invention, which are dilutable in all proportions with water, can be produced in the form of composition supports, optionally concentrated and containing, for example, from 1 to 40 percent by weight of wax. They are provided in the form of fluid compositions.

The concentrated cosmetic composition supports can be diluted at the time of use, so as to obtain a wax concentration ranging, for example, from 0.1 to 10 percent by weight.

There can also be added (after dilution, in the case of concentrated compositions) the secondary ingredients.

The cosmetic composition supports obtained in accordance with the present invention are then, on the one hand, concentrated microdispersions mentioned above to be diluted at the time of use, and on the other hand non-concentrated microdispersions (containing at least water, the wax and the surfactant) to which can be added at the time of use, the secondary ingredients defined above.

The present invention also relates to a process for cosmetically treating the hair so as to improve the hold and volume of the hair style and/or to suppress or retard the onset of an oil appearance of the hair, characterized by the fact that there is applied, at least on the portion of the hair near the roots, an amount sufficient to impregnate the hair or the portions of the hair to be treated, a composition such as defined above, after optional dilution so that the weight amount of wax in the composition is from 0.1 to 20 percent. The optional dilution is indeed effected with water which can also contain hydrosoluble ingredients so as to obtain the desired composition.

This process of cosmetically treating the hair is carried out as has been indicated above.

The following non-limiting examples illustrate the present invention.

The compositions described in the examples of preparation A to L can be employed as cosmetic composition supports, or as a hair lotion, after dilution, if necessary, and after optional pH adjustment.

EXAMPLE A

A mixture of 10g of Carnauba wax and 1.84 g of a nonionic surfactant, resulting from the polyaddition of 3 moles of glycidol to 1 mole of nonylphenol is heated to 90° C. and the mixture is homogenized by gentle stirring. There are incorporated, with stirring, 88.16 g of water heated to 90° C. The resulting microemulsion is then returned to ambient temperature thereby forming a microdispersion of particles based on the wax.

Average diameter of the wax particles: 99 nm.

EXAMPLE B

The procedures set forth in Example A are repeated except that the surfactant in this example consists of 1 g of potassium oleate and 1 g of sodium oleate. The amount of water employed (88 g) is that which provides 100 g of the microemulsion.

A wax microdispersion is obtained wherein the average diameter of wax particles is 71 nm.

EXAMPLE C

In an analogous manner, a microdispersion containing 15 percent of Carnauba wax and 7.7 percent of triethanolamine oleate is produced.

The average diameter of wax particles is 73 nm.

EXAMPLE D

In an analogous manner, a wax microdispersion containing 10 percent Carnauba wax and 1.8 percent sodium dodecylsulfate is produced.

The average diameter of wax particles is 202 nm.

On replacing the sodium dodecylsulfate with 2.2 percent of sodium dodecylbenzene sulfonate, the average diameter of the wax particles is 277 nm.

EXAMPLE E

In an analogous manner, wax microdispersions are produced containing 10 percent Carnauba wax and respectively x percent of nonionic emulsifier.

| Emulsifier | x | Average diameter (nm) |
|---|---|---|
| Brij 98 | 2.4 | 108 |
|  | 3.6 | 67 |
|  | 4.8 | 46 |
| Brij 78 | 4.2 | 61 |
| Brij 58 | 4.7 | 39 |
| Myrj 51 | 6.75 | 111 |
| Myrj 52 | 8.6 | 74 |
| Tween 40 | 5.3 | 81 |
| Tween 60 | 5.4 | 69 |
| Tween 80 | 5.4 | 66 |

Brij 78 is octadecanol polyoxyethylenated with 20 moles of ethylene oxide.

Brij 98 is octadecene-1-ol polyoxyethylenated with 20 moles of ethylene oxide.

Brij 58 is hexadecanol polyoxyethylenated with 20 moles of ethylene oxide.

Myrj 51 is stearic acid polyoxyethylenated with 30 moles of ethylene oxide.

Myrj 52 is stearic acid polyoxyethylenated with 40 moles of ethylene oxide.

Tween 40 is sorbitol palmitate polyoxyethylenated with 20 moles of ethylene oxide.

Tween 60 is sorbitol stearate polyoxyethylenated with 20 moles of ethylene oxide Tween 80 is sorbitol oleate polyoxyethylenated with 20 moles of ethylene oxide.

EXAMPLE F

In an analogous manner, microdispersions having 15 percent Carnauba wax and respectively x percent of nonionic emulsifier are produced.

| Emulsifier | x | Average diameter (nm) |
|---|---|---|
| Brij 98 | 3.6 | 102 |
|  | 7.2 | 52 |
|  | 10.8 | 34 |

EXAMPLE G

In an analogous manner a wax microdispersion containing 20 percent Carnauba wax and 4.8 percent Brij 98 is produced.

The average diameter of the particles is 108 nm.

EXAMPLE H

In an analogous fashion, a wax microdispersion containing 25 percent Carnauba wax and 11.95 percent Brij 98 as the nonionic emulsifier is produced.

The average diameter of the particles is 36 nm.

EXAMPLE I

In an analogous manner, wax microdispersions containing 10 percent, 15 percent or 20 percent of Carnauba wax and respectively x percent of nonionic emulsifier (NI) are produced.

| Wax | Emulsifier | x | Average diameter (nm) |
|---|---|---|---|
| 10% | NI 1 | 2.7 | 104 |
|  | NI 2 | 2.9 | 147 |
|  | NI 3 | 3.0 | 106 |
|  | NI 4 | 3.2 | 190 |
|  | NI 5 | 1.8 | 96 |
|  | NI 6 | 5.2 | 257 |
|  | NI 7 | 5.4 | 343 |
|  | NI 8 | 4.74 | 314 |
| 15% | NI 2 | 4.4 | 171 |
|  | NI 3 | 4.5 | 131 |
|  | NI 4 | 4.85 | 213 |
|  | NI 9 | 2.8 | 145 |
|  | NI 5 | 2.1 | 145 |
|  |  | 2.8 | 105 |
|  |  | 3.45 | 80 |
|  |  | 4.1 | 78 |

-continued

| Wax | Emulsifier | x | Average diameter (nm) |
|---|---|---|---|
| 20% | NI 2 | 5.9 | 211 |
|  | NI 5 | 3.7 | 96 |

NI 1 is oleylic alcohol polyglycerolated with 5 moles of glycerol.

NI 2 is oleocetyl alcohol polyglycerolated with 6 moles of glycerol.

NI 3 is isostearyl alcohol polyglyerolated with 6 moles of glycerol.

NI 4 is 1,2-octadecanediol polyglycerolated with 7 moles of glycerol.

NI 5 is nonylphenol polyglycerolated with 3.25 moles of glycerol.

NI 6 is the 1-octylether of 1,2-hexadecanediol polyglycerolated with 12 moles of glycerol.

NI 7 is the 1-octylether of 1,2-octadecanediol polyglycerolated with 12 moles of glycerol.

NI 8 is the 1-octylether of 1,3-octadecanediol polyglycerolated with 10 moles glycerol.

NI 9 is nonylphenol polyglycerolated with 3 moles of glycerol.

EXAMPLE J

In an analogous manner, microdispersions containing 10% Candedilla wax and respectively x% of emulsifier are produced.

| Emulsifier | x | Average diameter (nm) |
|---|---|---|
| Potassium oleate | 2.0 | 139 |
| Brij 98 | 4.8 | 289 |
| NI 5 | 1.8 | 157 |

EXAMPLE K

The starting product employed is a self-emulsifiable wax sold by Tisoco under the trade name "Cire Autolustrate OFR", which consists of a mixture of Carnauba wax and paraffin wax in the presence of nonionic emulsifiers.

12 g of the starting product are heated near to 90° C. with homogenization. 88 g of water at the same temperature are added with stirring.

The mixture is permitted to cool to ambient temperature thereby resulting in the wax microdispersion.

The average diameter of the particles is 150 nm.

EXAMPLE L

The starting product employed is a self-emulsifiable wax sold by La Ceresine under the trade name "Cerax A.0. 28/B" which consists of a vegetable wax of Alfa in admixture with a nonionic emulsifier.

120 g of this mixture are heated to about 90° C. with homogenization by gentle stirring. 880 g of water at a temperature of about 90° C. are incorporated with stirring.

The mixture is then cooled to ambient temperature thereby resulting in the wax microdispersion.

The average diameter of the particles is 250 nm.

EXAMPLE M

There are prepared, in a manner analogous to that described in Example A, wax microdispersions having the following compositions:

| Carnauba wax | x % |
|---|---|
| Oil | y % |
| Potassium oleate | 3.33% |
| Water | 86.67% | with $x + y = 10$.

The results are set forth in the following table:

| Example | Wax x | Oil y | Average diameter (nm) |
|---|---|---|---|
|  | Carnauba | Paraffin |  |
| M1 | 9 | 1 | 47 |
| M2 | 7 | 3 | 88 |
|  | Carnauba | DV* |  |
| M3 | 9 | 1 | 55 |
| M4 | 7 | 3 | 77 |
|  | Carnauba | Turnsole |  |
| M5 | 9 | 1 | 55 |
| M6 | 7 | 3 |  |

*DV: 3-(2-ethylhexyloxy)-1-hexadecanoyloxy-2-propanol, described in French patent 2.222.351.

EXAMPLE N

In an analogous manner, wax microdispersions having the following weight composition are prepared.

| Carnauba wax | 10% |
|---|---|
| Lipophilic additive | x % |
| Brij 58 | 2.5% |
| Water, sufficient amount for | 100% |

The microdispersion is prepared in accordance with the procedures set forth in Example A. The lipophilic additive is mixed with the other ingredients before the addition of water.

| Example | Lipophilic Additive | x | Average diameter, nm |
|---|---|---|---|
| N1 | Parsol MCX | 3 | 141 |
| N2 | Parsol MCX | 2.4 | 132 |
|  | Uvinul M40 | 0.6 |  |

Parsol MCX is the commercial name of octyl methoxycinnamate, sold by Givaudan.

Uvinul M 40 is the commercial name of benzophenone-3, sold by BASF.

EXAMPLE O

Wax microdispersion having the following weight composition are prepared:

| Carnauba wax | x % |
|---|---|
| Oil | y % |
| Brij 98 | 4.78% |
| Water | 85.22% | with $x + y = 10$

The microdispersions are prepared in accordance with the procedures set forth in Example A. The oil is added to the wax before the introduction of the water.

| Example | Wax x | Oil y | Average diameter (nm) |
|---|---|---|---|
|  | Carnauba | Paraffin |  |

-continued

| Example | Wax x | Oil y | Average diameter (nm) |
|---|---|---|---|
| 01 | 9.5 | 0.5 | 46 |
| 02 | 9 | 1 | 46 |
| 03 | 8.5 | 1.5 | 46 |
| 04 | 8 | 2 | 49 |
| 05 | 7.5 | 2.5 | 49 |
| 06 | 7 | 3 | 48 |
|   | Carnauba | DV* | |
| 07 | 9 | 1 | 48 |
| 08 | 7 | 3 | 72 |
|   | Carnauba | Turnsole | |
| 09 | 9 | 1 | 52 |
| 010 | 7 | 3 | 290 |

*See Example M

EXAMPLE P

Wax microdispersions having the following weight composition are prepared:

| Carnauba wax | x % |
|---|---|
| Ceramide and/or cholesterol | y % |
| Potassium oleate | 3.33% |
| Water | 86.67% |
| with x + y = 10 | |

These microdispersions are prepared in accordance with the procedures set forth in Example A.

| Example | Wax x | Lipophilic Compound, y | Average Diameter (nm) |
|---|---|---|---|
|   | Carnauba | DVA | |
| P1 | 8 | 2 | 108 |
|   | Carnauba | Cholesterol | |
| P2 | 9 | 1 | 118 |
| P3 | 8 | 2 | 218 |
|   | Carnauba | +DVA:1 | |
| P4 | 8 | +Cholesterol:1 | 167 |

DVA: Ceramide of the formula:
$C_{15}H_{31}CHOH.CHCH_2OH$
              |
              $NHCOC_{15}H_{31}$
erythro: threo mixture

EXAMPLE Q

In an analogous manner wax microdispersions having the following weight composition are prepared:

| Carnauba wax | x % |
|---|---|
| Ceramide or cholesterol | y % |
| Brij 58 | 2.34% |
| Water | 87.66% |
| with x + y = 10 | |

| Example | Wax x | Lipophilic Compound, y | Average Diameter (nm) |
|---|---|---|---|
|   | Carnauba | DVB | |
| Q1 | 9 | 1 | 105 |
| Q2 | 8 | 2 | 127 |
| Q3 | 7 | 3 | 170 |
|   | Carnauba | DVA | |
| Q4 | 8 | 2 | 92 |
|   | Carnauba | Cholesterol | |
| Q5 | 9 | 1 | 136 |

DVA: See Example P
DVD: Ceramide of the same formula as DVA, but in erythro form only.

EXAMPLE R

In an analogous manner, wax microdispersions having the following weight composition are prepared:

| Carnauba wax | x % |
|---|---|
| Ceramide and cholesterol | y % |
| Brij 58 | 2.34% |
| Water | 87.66% |
| with x + y = 10 | |

| Example | Wax x Carnauba | Lipophilic Compound, y DVA:1 | Average Diameter (nm) |
|---|---|---|---|
| R | 8 | +Cholesterol:1 | 96 |

EXAMPLE S

In an analogous manner, wax microdispersions having the following weight composition are prepared:

| Carnauba wax | 10% |
|---|---|
| Lipophilic additive | x % |
| Potassium oleate | 3.33% |
| Water, sufficient amount for | 100% |

| Example | Lipophilic Additive, x | Average Diameter (nm) |
|---|---|---|
| S1 | Colorant* 1% | 43 |
| S2 | Parsol MCX 3% | 254 |
| S3 | Parsol MCX 2.4% Uvinul M40 0.6% | 155 |

*2-isopropyl-6-nitro aniline

EXAMPLES OF PREPARING COSMETIC COMPOSITIONS

EXAMPLE 1

The following before-shampoo care composition is prepared by incorporating in the wax microdispersion the other constituents, in the order indicated:

| Wax microdispersion obtained in Example L | 98 g |
|---|---|
| Hydroxypropylmethylcellulose, sold by Dow Chemical under the trade name "Methocel F4M" | 1.5 g |
| Methyl paraphydroxybenzoate | 0.2 g |
| Derivative of imidazolidinyl urea, sold by Sutton Labs under the trade name "Germall 115" | 0.3 g |

This composition is applied to dry and non-washed hair, strand by strand on the hair roots. The composition is permitted to remain in contact with the hair for 2 to 5 minutes. Thereafter the hair is rinsed with water and the hair is shampooed.

The amount applied is about 2 g/head.

The application of this before-shampooing composition imparts to the hair elasticity, shine, softness and volume.

EXAMPLE 2

The following fluid hair styling gel is prepared by incorporating in the wax microdispersion the other ingredients in the order indicated:

| | |
|---|---|
| Wax microdispersion obtained in Example L | 20 g |
| Crosslinked polyacrylic acid (MW = 1,250,000), sold by Goodrich under the trade name "Carbopol 941" | 1 g |
| Derivatives imidazolidinyl urea, sold under the trade name "Germall 115" by Sutton Labs | 0.3 g |
| Sodium hydroxide, sufficient amount for pH = 7 | |
| Water, sufficient amount for | 100 g |

This composition is applied to clean and dry hair, at the roots and throughout the length of the hair, at a rate of 2 to 5 g per head according to the abundance of the hair. The product is spread easily and in a homogeneous manner onto the hair and imparts thereto softness, volume, fullness and control.

EXAMPLE 3

The following hair styling lotion is prepared by incorporating in the wax microdispersion the other constituents in the order indicated:

| | |
|---|---|
| Microdispersion of 10% Carnauba wax prepared in accordance with Example A | 99.65 g |
| Methyl parahydroxybenzoate | 0.15 g |
| Derivative of imidazolidinyl urea, sold under the trade name "Germall 115" by Sutton Labs | 0.20 g |

This composition is applied to clean and dry hair starting at the roots and along the length of the hair at a rate of 2 g/head (for an average feminine head of hair).

The hair thus treated has volume, thickness and hold and is controlled. Brushing reveals its fullness.

EXAMPLE 4

The following hair styling lotion is prepared by incorporating in the wax microdispersion the other constituents in the order indicated:

| | |
|---|---|
| Microdispersion of 10% Carnauba wax and 2.7% NI (see Example I) | 99.65 g |
| Methyl parahydroxybenzoate | 0.15 g |
| Derivative of imidazolidinyl urea, sold under the trade name "Germall 115" by Sutton Labs | 0.20 g |

This composition is used in completing a hair styling of clean and dry hair. The application is made on the roots of the hair and distributed on the length of the hair strands at a rate of 2 g/head.

The hair is shiny, full and light.

EXAMPLE 5

The following before-shampoo treatment composition is prepared by incorporating in the wax microdispersion the other constituents in the order indicated:

| | |
|---|---|
| Microdispersion of 10% Carnauba wax and 2.9% NI2 (see Example I) | 97.5 g |
| Hydroxypropylcellulose sold under the trade name "Klucel H" by Hercules | 2 g |
| Methylparahydroxybenzoate | 0.2 g |
| Derivative of imidazolidinyl urea, sold under the trade name "Germall 115" by Sutton Labs | 0.3 g |

This composition (about 2 g/head) is applied strand by strand on non-washed dry hair and is permitted to remain in contact with the hair for 5 minutes before shampooing the hair.

The application of this composition imparts to the hair volume (separation of the roots), smoothness and shine.

EXAMPLE 6

The following hair structuring lotion is prepared by incorporating in the wax microdispersion the other constituents in the order indicated:

| | |
|---|---|
| Microdispersion of 10% Carnauba wax and 3% NI 3 (see Example I) | 99.5 g |
| Methyl parahydroxybenzoate | 0.2 g |
| Derivative of imidazolidinyl urea, sold under the trade name "Germall 115" by Sutton Labs | 3 g |

This composition is intended for the completion of the hair style. Consequently it is applied to clean, dry hair at a rate of 2 to 3 g/head according to the abundance of hair being treated.

The composition rapidly dries and its distribution, principally on the hair roots, imparts to the hair style structure, volume and control.

EXAMPLE 7

A fluid hair styling gel having the following composition is prepared by incorporating in the wax microdispersion the other constituents in the order indicated:

| | |
|---|---|
| Wax microdispersion obtained in Example K | 10 g |
| Carbopol 941 | 1.5 g |
| NaOH | 0.6 g |
| PEG-15 Cocamine | 3 g |
| Germall 115 | 0.2 g |
| Methyl parahydroxybenzoate | 0.2 g |
| Potassium sorbate | 0.3 g |
| Perfume, sufficient amount | |
| Triethanolamine, sufficient amount for pH = 7 | |
| Water, sufficient amount for | 100 g |

PEG-115 Cocamine: Polyethyleneglycolamine of copra acid, according to the definition of CTFA (Cosmetic, Toiletry and Fragrance Association); product sold by Akzo under the commercial name "Ethomeen C25".

The gel is used in the manner set forth in Example 2.

EXAMPLE 8

This lotion is prepared by mixing in the order indicated the following constituents.

| | |
|---|---|
| Wax microdispersion obtained in Example M1 | 95 g |

-continued

| | |
|---|---|
| Methyl parahydroxybenzoate | 0.15 g |
| Derivative of imidazolidinyl urea, sold under the trade name "Germall 115" by Sutton Labs | 0.2 g |
| NaOH, sufficient amount for pH = 6.8 | |
| Water, sufficient amount for | 100 g |

The composition is applied to clean and dry hair. The treated hair is shiny and full.

EXAMPLE 9

The procedures of Example 1 are repeated using the following constituents:

| | |
|---|---|
| Wax microdispersion obtained in Example M4 | 98 g |
| Methyl parahydroxybenzoate | 0.1 g |
| Germall 115 | 0.25 g |
| NaOH, sufficient amount for pH = 7 | |
| Water, sufficient amount for | 100 g |

This composition is applied to the hair after a shampoo and the thus treated hair is shiny and controlled.

EXAMPLE 10

This lotion is prepared by mixing in the order indicated the following constituents:

| | |
|---|---|
| Was microdispersion obtained in Example N2 | 99.65 g |
| Methyl parahydroxybenzoate | 0.15 g |
| Germall 115 | 0.20 g |
| NaOH, sufficient amount for pH = 7 | |

This composition is applied to clean and dry hair. In addition to achieving the effects of volume, hold and control the composition imparts to the hair a protective effect vis-a-vis UV radiation.

EXAMPLE 11

The procedures of Example 1 are repeated using the following constituents:

| | |
|---|---|
| Wax microdispersion obtained in Example 07 | 95 g |
| Methyl parahydroxybenzoate | 0.15 g |
| Germall 115 | 0.2 g |
| NaOH, sufficient amount for pH = 6.9 | |
| Water, sufficient amount for | 100 g |

This composition is applied as in Example 9 and analogous results are obtained.

EXAMPLE 12

This lotion is prepared by mixing in the order indicated the following constituents:

| | |
|---|---|
| Wax microdispersion obtained in Example P4 | 50 g |
| Methyl parahydroxybenzoate | 0.15 g |
| Germall 115 | |
| NaOH, sufficient amount for pH = 7 | |
| Water, sufficient amount for | 100 g |

This composition is used after a shampoo. It imparts a protective effect to the hair which exhibits body and volume.

EXAMPLE 13

The procedures of the preceding example are repeated except that the microdispersion of Example P4 is replaced with that of Example Q5. Analogous results are obtained.

EXAMPLE 14

This lotion is prepared by mixing, in the order indicated, the following constituents:

| | |
|---|---|
| Wax microdispersion obtained in Example S1 | 98 g |
| Methyl parahydroxybenzoate | 0.1 g |
| Germall 115 | 0.1 g |
| NaOH, sufficient amount for pH = 6.8 | |
| Water, sufficient amount for | 100 g |

This composition is applied as in Example 3. Analogous effects on the hair are obtained. Moreover, the hair is colored yellow.

What is claimed is:

1. A process for the cosmetic treatment of hair so as (a) to improve the hold and volume of the style of the hair, or (b) to suppress or retard the appearance of an oily aspect of the hair, or both (a) and (b), said process comprising applying to at least a portion of the hair close to the roots thereof, in an amount sufficient to impregnate the hair or the portion of the hair being treated, a cosmetic composition comprising a non-foaming fluid composition containing a wax dispersion in a liquid vehicle containing from 80 to 100 percent water, the dispersed phase in said liquid vehicle being a stable microdispersion of particles having a size lower than 500 nm and comprising a wax, the said wax having an end melting point greater than 60° C. and lower than 100° C. and being capable of forming said microdispersion, said composition containing, by weight, from 1 to 20 percent of said wax, from 0.01 to 25 percent of at least one anionic or nonionic emulsifier and at least 35 percent of water, the wax/emulsifier weight ratio ranging from 1 to 30 and said composition not containing a cationic surfactant.

2. The process of claim 1 wherein said wax is selected from Carnauba wax, Candelilla wax, Alfa wax or a mixture thereof.

3. The process of claim 1 wherein said wax comprises Carnauba wax or Candelilla wax or a mixture thereof in combination with at least one other wax selected from paraffin wax, ozokerite, hydrogenated jojoba wax, rice wax, beeswax or a ceramide.

4. The process of claim 1 wherein said wax is present in an amount ranging from 1 to 20 weight percent based on the total weight of said composition.

5. The process of claim 3 wherein said Carnauba wax, or said Candelilla wax or said mixture thereof is present in said combination with said other wax in an amount greater than or equal to 50 weight percent.

6. The process of claim 1 wherein said emulsifier is present in an amount ranging from 0.1 to 10 weight percent.

7. The process of claim 1 wherein said nonionic emulsifier is a polyalkoxylated or polyglycerolated surfactant.

8. The process of claim 1 wherein said emulsifier is an anionic surfactant.

9. The process of claim 1 wherein said liquid vehicle is water.

10. The process of claim 1 wherein the weight ratio of wax to emulsifier ranges from 1 to 20.

11. The process of claim 1 wherein the weight ratio of wax to emulsifier ranges from 2 to 10.

12. The process of claim 1 wherein said cosmetic composition also includes at least one amphiphilic compound combined with said wax, said amphiphilic compound not being emulsifiable with said wax and being present in an amount up to 30 weight percent relative to the weight of said wax, said amphiphilic compound being cholesterol or a fatty alcohol having at least 12 carbon atoms.

13. The process of claim 12 wherein said amphiphilic compound is present in an amount up to 10 weight percent relative to the weight of said wax.

14. The process of claim 1 wherein said wax is present in an amount ranging from 1 to 10 weight percent based on the total weight of said composition.

15. The process of claim 1 wherein said composition includes, in combination with said wax, an oil or a mixture of oils in an amount ranging up to 30 weight percent relative to the weight of said wax.

16. The process of claim 15 wherein said oil or mixture of oils is present in an amount ranging up to 10 weight percent relative to the weight of said wax.

17. The process of claim 1 wherein said composition also includes, in combination with said wax, at lest one liposoluble active ingredient present in an amount ranging up to 30 weight percent relative to the weight of said wax.

18. The process of claim 17 wherein said liposoluble active ingredient is present in an amount ranging up to 10 weight percent relative to the weight of said wax.

19. The process of claim 17 wherein said liposoluble active ingredient is selected from a liposoluble dye or a liposoluble substance imparting a protective effect against the harmful effects of ultraviolet radiation.

* * * * *